United States Patent [19]

Stahly

[11] Patent Number: 5,175,302

[45] Date of Patent: Dec. 29, 1992

[54] NUCLEOPHILIC FLUOROALKYLATION OF ALDEHYDES

[75] Inventor: G. Patrick Stahly, Baton Rouge, La.

[73] Assignee: Ethyl Corporation, Richmond, Va.

[21] Appl. No.: 294,301

[22] Filed: Jan. 9, 1989

Related U.S. Application Data

[62] Division of Ser. No. 72,629, Jul. 13, 1987, Pat. No. 4,837,327.

[51] Int. Cl.⁵ .......................................... C07D 213/30
[52] U.S. Cl. ................................................ 546/344
[58] Field of Search ........................................ 546/344

[56] References Cited

U.S. PATENT DOCUMENTS 4,678,790  7/1987  Dorn et al. .......................... 546/344

Primary Examiner—Johann Richter
Attorney, Agent, or Firm—John F. Sieberth; Richard J. Hammond

[57] ABSTRACT

Aryl difluoromethyl sulfone adds to aldehydes under phase transfer conditions to give novel substituted alcohols of the general formula $$RCH(OH)CF_2SO_2Ar \qquad (I)$$

wherein R is an aryl, cycloaliphatic, sec- or tert-aliphatic, or heterocyclic group and Ar is an aryl group. The substituted alcohols of formula I are of particular utility as intermediates in the synthesis of a variety of useful end products. For example, the products of formula I may be utilized in desulfonylation reactions, oxidation reactions and fluorination reactions.

1 Claim, No Drawings

NUCLEOPHILIC FLUOROALKYLATION OF ALDEHYDES

This application is a division of application Ser. No. 07/072,629, filed Jul. 13, 1987 now U.S. Pat. No. 4,837,327.

TECHNICAL FIELD

This invention relates to a novel nucleophilic fluoroalkylation process, to the novel products so produced, and to novel reactions utilizing such products.

BACKGROUND

The synthesis of $\alpha, \beta$-unsaturated sulfones by phase transfer catalyzed condensation of sulfones with aldehydes in an aqueous system has been reported (Cardillo et al., *Synthesis,* 1975, 453–455). The sulfones employed were phenyl methyl sulfone phenyl ethyl sulfone, phenyl benzyl sulfone, phenyl 3-methylbuten-2-yl sulfone and methyl dimethylamino sulfone. They found that the choice of aldehyde was limited to aromatic or $\alpha, \beta$-unsaturated aldehydes, since aliphatic aldehydes and ketones underwent self-condensation under the reaction conditions while aromatic ketones (benzophenone, fluorenone) were unreactive. Triethylbenzylammonium chloride was used as the phase transfer catalyst, and the reactions were conducted in a two-phase system of water and dichloromethane. The sulfone products formed by Cardillo et al had the general formula

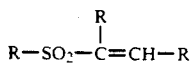

THE INVENTION

This invention involves, inter alia, the discovery that aryl difluoromethyl sulfone adds to aldehydes under phase transfer conditions to give novel substituted alcohols of the general formula

wherein R is an aryl, cycloaliphatic, sec- or tert-aliphatic, or heterocyclic group and Ar is an aryl group. The fact that this nucleophilic alkylation occurs is most unusual since in general compounds of the type $CHF_2X$ (where X is an electron withdrawing group) do not exhibit nucleophilic behavior, but eliminate HX to difluorocarbene. In fact, the only prior instance known to applicant as of this writing where an aryl difluoromethylsulfone was used as a nucleophile is the addition of difluoromethylphenyl sulfone in the presence of an alkali metal alkoxide to a steroid of the pregnane and 19-nor pregnane series having, as the only site of keto conjugated unsaturation the $\Delta^{16}$-20-keto functional system, whereby the corresponding 16 $\alpha$-(benzenesulfonyldifluoromethyl)-20-keto steroid is formed—see U.S. Pat. No. 3,705,182 to Edwards et al of Syntex Corporation.

Accordingly in one of its embodiments this invention provides a process which comprises reacting aryl difluoromethyl sulfone with one or more aldehydes under phase transfer condition so that a substituted alcohol of the above formula (I) is produced. In conducting this process any aldehyde can be used which reacts with aryl difluoromethyl sulfone at a rate competitive with the rates of other base-induced reactions of the aldehyde (aldol or Canizzarro reactions). Even if these other reactions compete, use of an excess of the aldehyde will often allow the desired alcoholic product to be obtained in satisfactory yield. Preferred aldehydes used in the process include aromatic aldehydes, cycloaliphatic aldehydes, secondary and tertiary aliphatic aldehydes, and heterocyclic aldehydes. The aldehyde reactant may contain any of a variety of substituents (chlorine, bromine, alkoxy, etc.) which do not inhibit the desired condensation reaction, but should not contain very strong electron withdrawing substituents such as the nitro group. A few illustrative examples of preferred aldehydes include 2-methylundecanal
p-acetamidobenzaldehyde
o-anisaldehyde
m-anisaldehyde
p-anisaldehyde
9-anthraldehyde
benzaldehyde
3-benzyloxybenzaldehyde
4-benzyloxybenzaldehyde
3-benzyloxy-4-methoxybenzaldehyde
4-benzyloxy-3-methoxybenzaldehyde
4-biphenylcarboxaldehyde
5-bromo-o-anisaldehyde
2-bromobenzaldehyde
3-bromobenzaldehyde
4-bromobenzaldehyde
5-bromoalicyclaldehyde
5-bromovanillin
6-bromoveratraldehyde
2-carboxybenzaldehyde
4-carboxybenzaldehyde
10-chloro-9-anthraldehyde
2-chlorobenzaldehyde
3-chlorobenzaldehyde
4-chlorobenzaldehyde
2-chloro-4-dimethylaminobenzaldehyde
2-chloro-6-fluorobenzaldehyde
2-chloro-5-nitrobenzaldehyde
3-cyanobenzaldehyde
4-cyanobenzaldehyde
3,4-dibenzyloxybenzaldehyde
3,5-dibromosalicylaldehyde
3,5-di-tert-butyl-4-hydroxybenzaldehyde
2,4-dichlorobenzaldehyde
2,6-dichlorobenzaldehyde
3,4-dichlorobenzaldehyde
3,5-dichlorobenzaldehyde
4-(diethylamino)-benzaldehyde
4-[$\beta$-(diethylamino)-ethoxy]-benzaldehyde
2,5-dihydroxybenzaldehyde
3,4-dihydroxybenzaldehyde
2,3-dimethoxybenzaldehyde
2,4-dimethoxybenzaldehyde
2,5-dimethoxybenzaldehyde
3,4-dimethoxybenzaldehyde
3,5-dimethoxybenzaldehyde
4,6-dimethoxysalicylaldehyde
p-dimethylaminobenzaldehyde
2,3-dimethyl-p-anisaldehyde
2,5-dimethyl-p-anisaldehyde
2,4-dimethylbenzaldehyde
2,5-dimethylbenzaldehyde
o-ethoxybenzaldehyde p-ethoxybenzaldehyde
3-ethoxy-4-hydroxybenzaldehyde
4-ethoxy-3-methoxybenzaldehyde
3-ethoxysalicyclaldehyde
N-ethyl-3-carbazolecarboxaldehyde
2-fluorenecarboxaldehyde
3-fluoro-p-anisaldehyde
o-fluorobenzaldehye
m-fluorobenzaldehyde
p-fluorobenzaldehyde
p-formylcinnamic acid
o-formylphenoxyacetic acid
5-formylsalicylic acid
helicin
3-hydroxy-p-anisaldehyde
3-hydroxybenzaldehyde
4-hydroxybenzaldehyde
2-hydroxy-4-methoxybenzaldehyde
2-hydroxy-5-methoxybenzaldehyde
2-hydroxy-1-naphthaldehyde
5-iodovanillin
isophthalaldehyde
mesitaldehyde
2-methoxy-1-naphthaldehyde
4-methoxy-1-naphthaldehyde
3-methyl-p-anisaldehyde
10-methylanthracene-9-carboxaldehyde
1-naphthaldehyde
2-naphthaldehyde
pentafluorobenzaldehyde
phenanthrene-9-carboxaldehyde
o-phthalicdicarboxaldehyde
piperonal
1-pyrenecarboxaldehyde
salicylaldehyde
syringaldehyde
terephthaldicarboxaldehyde
o-tolualdehyde
m-tolualdehyde
p-tolualdehyde
2,4,6-triethoxybenzaldehyde
2,3,4,-trimethoxybenzaldehyde
2,4,5-trimethoxybenzaldehyde
2,4,6-trimethoxybenzaldehyde
3,4,5-trimethoxybenzaldehyde
vanillin
o-vanillin
5-acetoxymethyl-2-furaldehyde
endo-bicyclo[3.1.0]hex-2-ene-6-carboxaldehyde
5-bromo-2-thiophenecarboxaldehyde
cyclohexanecarboxaldehyde
cyclooctanecarboxaldehyde
5,6-dihydro-2H-pyran-3-carboxaldehyde
ferrocenecarboxaldehyde
5-formyl-2-furansulfonic acid
2-furaldehyde
5-hydroxymethylfurfural
indole-3-carboxaldehyde
5-methoxyindole-3-carboxaldehyde
5-methylfurfural
6-methyl-1-pyridinecarboxaldehyde
N-methylpyrrole-2-carboxaldehyde
3-methyl-2-thiophenecarboxaldehyde
5-methyl-2-thiophenecarboxaldehyde
5-norbornene-2-carboxaldehyde
2-pyridinecarboxaldehyde
3-pyridinecarboxaldehyde
4-pyridinecarboxaldehyde
pyridoxal 5-phosphate monohydrate
pyrrole-2-carboxaldehyde
3-quinolinecarboxaldehyde
4-quinolinecarboxaldehyde
1,2,3,6-tetrahydrobenzaldehyde
2-thiophenecarboxaldehyde Of the aldehydes exemplified above, those that do not ionize under the reaction conditions used are preferred.

Aryl difluoromethyl sulfones suitable for use in the process are exemplified by
phenyl difluoromethyl sulfone
4-chlorophenyl difluoromethyl sulfone
o-tolyl difluoromethyl sulfone
m-tolyl difluoromethyl sulfone
p-tolyl difluoromethyl sulfone
4-methoxyphenyl difluoromethyl sulfone
2,4-dichlorophenyl difluoromethyl sulfone
2-bromophenyl difluoromethyl sulfone
4-fluorophenyl difluoromethyl sulfone
1-naphthyl difluoromethyl sulfone
2-naphthyl difluoromethyl sulfone
4-biphenylyl difluoromethyl sulfone
4-phenoxyphenyl difluoromethyl sulfone
4-diethylaminophenyl difluoromethyl sulfone Methods for the synthesis of such compounds are known and reported in the literature. See for example Hine et al., *J. Am. Chem. Soc.*, 1957, 79, 5493 and *Ibid*, 1960, 82, 6178. And applicant has found that conditions similar to those reported by Miller et al, *J. Org. Chem.*, 1960, 25, 2009 for the synthesis of difluoromethyl ethers can be successfully used for producing aryl difluoromethyl thioethers which on oxidation produce the aryl difluoromethyl sulfones. See Examples 1 and 2, infra.

As is well known, phase transfer conditions involve use of a two-phase reaction medium of water and a suitable organic solvent (hydrocarbon, chlorinated hydrocarbon, etc.), a strong base (alkali metal hydroxide or alkoxide, etc.) and a phase transfer catalyst such as a quaternary ammonium or phosphonium salt, a crown ether or the like. For further details concerning phase transfer systems that may be used in the practice of the above process, see, for example, Dehmlow, *Angew. Chem.*, 1977, 89, 521 and *Angew Chem. Int. Ed. Engl.*, 1977, 16, 493; Dehmlow, *Angew Chem.*, 1974, 86, 1087 and *Angew Chem. Int. Ed. Engl.*, 1974, 13, 170; Gokel et al., *J. Chem. Educ.*, 1978, 55, 350,439; Weber et al., *Phase Transfer Catalysis in Organic Synthesis*, Springer, Berlin, 1977; Starks et al., *Phase Transfer Catalysis: Principles and Techniques*, Academic Press, New York, 1978; Dehmlow et al., *Phase Transfer Catalysis*, 2nd Edition, Verlag Chemie, Weinheim, 1983, disclosures of which are incorporated herein by reference.

The reaction temperature is generally in the range of about 0° to about 100° C., and preferably in the range of about 20° to about 30° C.

Proportions of the reactants, solvents, and catalyst are not critical and can be varied to suit the needs of the occasion. Since the desired reaction involves the stoichiometric condensation between the sulfone and the aldehyde, it is desirable to employ the reactants in approximately equivalent amounts on a molar basis. As noted above, use of excess aldehyde is beneficial in instances where base-induced competitive reactions of aldehyde occur in the system. Any reasonable excess of aldehyde can be employed as the extent of the desired reaction will thus be limited by the amount of sulfone reactant employed.

To insure intimate contact of the reactants in the reaction mixture, the reaction system should be subjected to stirring, shaking or other physical forms of agitation.

A few of the noval sulfonyl-substituted 2,2-difluoroethanols (Formula I above) provided by this invention are the following:

2,2-difluoro-1-phenyl-2-phenylsulfonylethanol
2,2-difluoro-2-phenylsulfonyl-1-(p-tolyl)ethanol
2,2-difluoro-2-phenylsulfonyl-1-(m-tolyl)ethanol
2,2-difluoro-2-phenylsulfonyl-1-(o-tolyl)ethanol
2,2-difluoro-1-(p-methoxyphenyl)-2-phenylsulfonylethanol
2,2-difluoro-1-(p-dimethylaminophenyl)-2-phenylsulfonylethanol
1-(2-chlorophenyl)-2,2-difluoro-2-phenylsulfonylethanol
2,2-difluoro-2-phenylsulfonyl-1-(2,4,6-trichlorophenyl)ethanol
1-(4-bromophenyl)-2,2-difluoro-2-phenylsulfonylethanol
2,2-difluoro-2-phenylsulfonyl-1-(2-trifluoromethylphenyl)ethanol
1-(p-acetamidophenyl)-2,2-difluoro-2-phenylsulfonylethanol
2,2-difluoro-1-(2,5-dimethoxyphenyl)-2-phenylsulfonylethanol
2,2-difluoro-1-(2-fluorophenyl)-2-phenylsulfonylethanol
2,2-difluoro-1-(1-naphthyl)-2-phenylsulfonylethanol
2,2-difluoro-1-(2-naphthyl)-2-phenylsulfonylethanol
2,2-difluoro-1-(pentafluorophenyl)-2-phenylsulfonylethanol
2,2-difluoro-1-(2-phenoxyphenyl)-2-phenylsulfonylethanol
1-(9-anthryl)-2,2-difluoro-2-phenylsulfonylethanol
2,2-difluoro-2-(2,4,6-mesitylsulfonyl)-1-phenylethanol
2,2-difluoro-1-phenyl-2-(o-tolylsulfonyl)ethanol
2,2-difluoro-1-(p-tolyl)-2-(2,4-xylylsulfonyl)ethanol
2,2-difluoro-1-(pentafluorophenyl)-2-(pentafluorophenylsulfonyl)ethanol
2,2-difluoro-2-(1-naphthylsulfonyl)-1-(4-trifluoromethylphenyl)ethanol
2,2-difluoro-2-(4-phenoxyphenylsulfonyl)-1-phenylethanol
2,2-difluoro-1-(2-furyl)-2-phenylsulfonylethanol
1-(5-acetoxymethyl-2-furyl)-2,2-difluoro-[2-phenylsulfonylethanol
1-(5-bromo-2-thiophene-1-yl)-2,2-difluoro-2-phenylsulfonylethanol
2,2-difluoro-1-(3-indole-1-yl)-2,2-difluoro-2-phenylsulfonylethanol
2,2-difluoro-2-phenylsulfonyl-1-(2-pyridine-1-yl)ethanol
1,1-difluoro-3-methyl-1-phenylsulfonyl-2-butanol
1,1-difluoro-3,3-dimethyl-1-phenylsulfonyl-2-butanol
1,1-difluoro-1-phenylsulfonyl-3,3,4-trimethyl-2-pentanol
1,1-difluoro-1-phenylsulfonyl-3,3,5,5-tetramethyl-2-hexanol
1-cyclohexyl-2,2-difluoro-2-phenylsulfonylethanol
1-cyclopentyl-2,2-difluoro-2-(o-tolyl)ethanol
2,2-difluoro-1-(5-hydroxymethyl-2-furyl)-2-phenylsulfonylethanol
2,2-difluoro-1-(N-methylpyrrole-2-yl)-2-phenylsulfonylethanol The following examples illustrate the practice of the above condensation process and some of the novel compounds that can be so produced. Examples 1 and 2 illustrate the synthesis of a preferred sulfone reactant and Examples 3-10 illustrate its use in the condensation process of this invention.

EXAMPLE 1

Difluoromethyl Phenyl Sulfide

A 6 ounce Fisher-Porter bottle was charged with 10.0 g (250 mmol) of sodium hydroxide, 13 mL of water, 15 mL of paradioxane, and 5.5 mL (54 mmol) of thiophenol. The bottle and overhead system were closed, the rapidly stirred mixture was heated to 60°-70° C. by means of an oil bath, and the system was charged to 50 psig with chlorodifluoromethane. Heating was continued for 1 hour, during which time the pressure gradually decreased and the system was occasionally recharged to 50 psig with chlorodifluoromethane. After cooling to room temperature, the system was opened and the reaction mixture was treated with 50 mL of water and 25 mL of diethyl ether. Filtration through glass wool paper followed by removal of the ether layer afforded an aqueous solution that was extracted with three 15 mL portions of diethyl ether. The ether layers were combined and concentrated in vacuo to give a residue which was dissolved in 50 mL of pentane. The pentane solution was washed with five 10 mL portions of water dried (MgSO$_4$), and concentrated in vacuo. Short path distillation of the residue gave 5.88 g (69% yield) of difluoromethyl phenyl sulfide: bp 24°-26° C. (1 torr): $^1$H NMR (CDCl$_3$) 6.80 (t, 1H, $J_{HF}=57$ Hz), 7.30-7.68 (m, 5H).

EXAMPLE 2

Difluoromethyl Phenyl Sulfone

A solution of 2.0 g (12 mmol) of difluoromethyl phenyl sulfide in 20 mL of dichloromethane was cooled to 0°-5° C. and treated portionwise with 5.4 g (27 mmol) of 85% meta-chloroperbenzoic acid. The mixture was allowed to warm to room temperature, stirred for 4 hours, treated with an additional 1.1 g (5.4 mmol) of 85% meta-chloroperbenzoic acid, and stirred overnight. Filtration and washing of the filter cake with 30 mL of dichloromethane gave a solution which was washed with three 25 mL portions of saturated NaHCO$_3$ and one 25 mL portion of water, dried (MgSO$_4$), and concentrated in vacuo. The residue was purified by flash chromatography on 50 g of silica gel (eluted with 25% dichloromethane, 75% petroleum ether) to give 1.92 g (83% yield) of difluoromethyl phenyl sulfone as a colorless liquid: IR (neat 3069, 1771, 1447, 1348, 1301, 1162, 1113, 1077, 760, 725, 685, 621, 606, 557, 545, 515, cm$^{-1}$; $^1$H NMR (CDCl$_3$) δ6.29 (t, 1H, $J_{HF}=54$Hz), 7.50-8.10 (m, 5H); mass spectrum (70 eV) m/e (relative intensity) 192 (22, M+), 141 (45), 77 (100), 51 (54).

EXAMPLE 3

2,2-Difluoro-1-phenyl-2-phenylsulfonylethanol

A mixture of 100 mg (0.52 mmol) of difluoromethyl phenyl sulfone 1.5 mL of dichloromethane, 1.0 mL of 50% sodium hydroxide in water, and one drop of Aliquat ® 336 (Aliquat is a registered trademark of Henkel Corporation—Aliquat 336 is tricaprylylmethylammonium chloride) was stirred vigorously for 10 minutes and treated with a solution of 0.16 mL (1.6 mmol) of benzaldehyde in 0.5 mL of dichloromethane. Vigorous stirring was continued for 3.5 hours and the resulting gel-like mixture was poured into 20 m of 1N HCl. Extraction of the aqueous mixture with two 10 mL portions of dichloromethane followed by combination, drying (MgSO$_4$), and concentration in vacuo of the organic layers gave a residue which was purified by preparative TLC (one 2 mm silica gel plate eluted with dichloromethane), affording 94 mg (61% yield) of 2,2-difluoro-1-phenyl-2-phenylsulfonylethanol as a semisolid; IR (neat) 3503, 3064, 2922, 1447, 1335, 1312, 1197, 1154, 1113, 1089 996, 738, 715, 698, 685, 585, 558, cm$^{-1}$; 1H NMR (CDCl$_3$) δ 3.54 (broad s, 1H), 5.54 (dd, 1H, JHF=21, 2Hz), 7.20-8.10 (m, 10H); $^{19}$F NMR (CDCl$_3$, relative to external CF$_3$CO$_2$H) −26.50 ppm (dd, 1F, $J_{FF}$=238 Hz, $J_{HF}$=2 Hz, −41.68 ppm (dd, 1F, $J_{FF}$=238 Hz, $J_{HF}$=21 Hz); mass spectrum (70 eV) m/e (relative intensity) 298 (8, M$^+$), 156 (18), 109 (31), 107 (100), 79 (30), 78 (18), 77 (56), 51 (20).

EXAMPLE 4

2,2-Difluoro-1-phenyl-2-phenylsulfonylethanol

A mixture of 100 mg (0.52 mmol) of difluoromethyl phenyl sulfone, 1.0 mL of dichloromethane, 1.0 mL of 50% aqueous sodium hydroxide and 20 mg (0.050 mmol) of Aliquat 336 was stirred vigorously for 10 minutes and treated with a solution of 0.16 mL (1.6 mmol) of benzaldehyde in 0.5 mL of dichloromethane. Vigorous stirring was continued for four hours and the resulting mixture was poured into 20 mL of 1N HCL. Extraction of the aqueous mixture with three 10 mL portions of dichloromethane followed by combination, drying (MgSO$_4$), and concentration in vacuo of the organic layers gave a residue which was purified by preparative TLC (two 2 mm silica gel plates eluted with dichloromethane), affording 140 mg (90% yield) of 2,2-difluoro-1-phenyl-2-phenylsulfonylethanol as a solid. Crystallization from toluene provided an analytical sample: mp 77°-79° C.; IR (neat) 3503, 3064, 2922, 1447, 1335, 1312, 1197, 1154, 1113, 1089, 996, 738, 715, 698, 685, 585, 558, cm$^{-1}$; $^1$H NMR (CDCl$_3$) δ 3.54 (broad s, 1H), 5.54 (dd, 1H $J_{HF}$=21, 3 Hz), 7.20-8.10 (m, 10H); $^{19}$F NMR (CDCl$_3$, relative to CFCl$_3$) −106.4 ppm (dd, 1F, $J_{FF}$=238 Hz, $J_{HF}$=3Hz), −121.6 ppm (dd, 1F, $J_{FF}$=238 Hz, $J_{HF}$=21 Hz); mass spectrum (70 eV) m/e (relative intensity) 298 (8, M$^+$), 156(18), 109(31), 107(100), 79(30), 78(18), 77(56), 51(20). Anal. Calcd. for C$_{14}$H$_{12}$F$_2$O$_3$S:C, 56.37; H, 4.06. Found: C, 56.58; H, 4.08.

EXAMPLE 5

2,2-Difluoro-1-(4-methoxyphenyl)-2-phenylsulfonylethanol

From 100 mg (0.52 mmol) of difluoromethyl phenyl sulfone 0.20 mL (1.6 mmol) of 4-methoxybenzaldehyde, 1.5 mL of dichloromethane, 1 mL of 50% aqueous sodium hydroxide and 20 mg (0.050 mmol) of Aliquat 336 was obtained 152 mg (89% yield) of 2,2-di-fluoro-1-(4-methoxyphenyl)-2-phenylsulfonylethanol as a solid. Crystallization from toluene provided an analytical sample: mp 93°-95° C.; IR (KBr) 3512, 3062, 2932, 1608, 1511, 1447, 1328, 1313, 1249, 1180, 1158, 1116, 1085, 1029, 995, 792, 683, 600, 595, 579, cm$^{-1}$; $^1$H NMR (CDCl$_3$) δ3.62 (d, 1H, J=3Hz), 3.77 (s, 3H), 5.50 (apparent dt, J=21, 3Hz), 6.80-7.02 (m, 2H), 7.26-8.13 (m, 7H); $^{19}$F NMR (CDCl$_3$, relative to CFCl$_3$) −104.6 ppm (dd, 1F,$J_{FF}$=236 Hz, $J_{HF}$=2 Hz), −119.9 ppm (dd, 1F, $J_{FF}$=237 Hz, $J_{HF}$=2 Hz); mass spectrum (70 eV) m/e (relative intensity) 328 (12, M$^+$), 137(100), 109(20), 77(20). Anal. Calcd. for C$_{15}$H$_{14}$F$_2$O$_4$S: C, 54.87; H, 4.30. Found: C, 54.90; H, 4.33.

EXAMPLE 6

2,2-Difluoro-1-(4-methylphenyl)-2-phenylsulfonylethanol

From 100 mg (0.52 mmol) of difluoromethyl phenyl sulfone 0.19 mL (1.6 mmol) of 4-methylbenzaldehyde, 1.5 mL of dichloromethane, 1 mL of 50% aqueous sodium hydroxide and 20 mg (0.050 mmol) of Aliquat 336 was obtained 129 mg (80% yield) of 2,2-di-fluoro-1-(4-methylphenyl)-2-phenylsulfonylethanol as a solid. Crystallization from toluene provided an analytical sample: mp 98°-100° C.; IR (KBr) 3534, 3059, 3031, 2920, 1450, 1325, 1314, 1159, 1106, 1087, 1002, 782, 722, 683, cm$^{-1}$; $^1$H NMR (CDCl$_3$) δ 2.35 (s, 3H), 3.38 (d, 1H, J=3 Hz), 5.51 (apparent dt, 1H, J=21, 3 Hz), 7.10-8.10 (m, 9H); $^{19}$F NMR (CDCl$_3$, relative to CFCl$_3$) −104.5 ppm (dd, 1F, $J_{FF}$=237 Hz, $J_{HF}$=2 Hz), −119.7 ppm (dd, 1F, $J_{FF}$=238 Hz, $J_{HF}$=21 Hz); mass spectrum (70 eV) m/e (relative intensity) 312 (6, M$^+$), 121(100), 93(20), 77(26). Anal. Calcd. for C$_{15}$H$_{14}$F$_2$O$_3$S: C, 57.68; H, 4.52. Found: C, 57.62; H, 4.66.

EXAMPLE 7

1-(4-Chlorophenyl)-2,2-difluoro-2-phenylsulfonylethanol

A reaction mixture generated from 100 mg (0.52 mmol) of difluoromethyl phenyl sulfone, 225 mg (1.6 mmol) of 4-chlorobenzaldehyde, 1.5 mL of dichloromethane, 1 mL of 50% aqueous sodium hydroxide and 20 mg (0.050 mmol) of Aliquat 336 was poured into 20 mL of 1N HCl. Extraction of the aqueous mixture with three 10 mL portions of ethyl acetate followed by combination, drying (MgSO$_4$), and concentration in vacuo of the organic layers gave a residue which was purified by preparative TLC (two 2 mm silica gel plates eluted with 10% ethyl acetate in toluene), affording 153 mg (88% yield) of 1-(4-chlorophenyl)-2,2-difluoro-2-phenylsulfonylethanol as a solid. Crystallization from toluene provided an analytical sample: mp; 100°-102° C.; IR (KBr) 3530, 3060, 2921, 1491, 1446, 1332, 1157, 1120, 1113, 1090, 1016, 1005, 784, 723, 683, 589, 538 cm$^{-1}$; $^1$H NMR (CDCl$_3$) δ3.62 (broad s, 1H), 5.56 (dd, 1H, J=20, 3 Hz), 7.26-8.13 (m, 9H); $^{19}$F NMR (CDCl$_3$, relative to CFCl$_3$ −104.8 ppm (dd, 1F, $J_{FF}$=238 Hz, $J_{HF}$=3 Hz), −119.2 ppm (dd, 1F, $J_{FF}$=238 Hz, $J_{HF}$=20 Hz); mass spectrum (70 eV) m/e (relative intensity) 332 (9, M$^+$), 143(44), 141(100, 77(33). Anal. Calcd. for C$_{14}$H$_{11}$ClF$_2$O$_3$S: C, 50.53; H, 3.33. Found: C, 50.49; H, 3.41.

EXAMPLE 8

α-(Difluoro[phenylsulfonyl]methyl)-2-furanmethanol

From 100 mg (0.52 mmol) of difluoromethyl phenyl sulfone 0.13 mL (1.6 mmol) of 2-furaldehyde, 1.5 mL of dichloromethane, 1 mL of 50% aqueous sodium hydroxide, and 20 mg (0.050 mmol) of Aliquat 336 was obtained a product mixture which was subjected to preparative TLC (two 2 mm silica gel plates eluted with dichloromethane), affording a mixture of α-(difluoro[phenylsulfonyl]-methyl)-2-furanmethanol and 2-furanmethanol. The mixture was dissolved in 5 mL of toluene and the resulting solution was washed with three 5 mL portions of water. Drying (MgSO$_4$) and concentration in vacuo of the toluene layer gave 121 mg (81% yield)

of α-(difluoro[phenylsulfonyl]methyl)-2-furanmethanol as a solid. Crystallization from toluene provided an analytical sample: mp 72°–74° C.; IR (KBr) 3501, 3114, 2943, 1448, 1338, 1314, 1201, 1161, 1107, 1089, 1078, 1065, 1017, 994, 924, 800, 770, 757, 711, 686, 600, 586, 532, cm$^{-1}$; $^1$H NMR (CDCl$_3$) δ 3.24 (broad s, 1H); 5.66 (dd, 1H, J=17 Hz, 4 HZ), 6.41–6.69 (m, 2H), 7.48–8.20 (m, 6H); $^{19}$F NMR (CDCl$_3$, relative to CFCl$_3$) −106.7 ppm (dd, 1F, $J_{FF}$=237 Hz, $J_{HF}$=4Hz); −116.7 ppm (dd, 1F, $J_{FF}$=237 Hz, $J_{HF}$=17 Hz); mass spectrum (70 eV) m/e (relative intensity) 288 (5, M+), 97(100), 77(20), 51(20), Anal. Calcd. for C$_{12}$H$_{10}$F$_2$O$_4$S: C, 50.00; H, 3.50. Found: C, 49.87; H, 3.59.

EXAMPLE 9

1,1-Difluoro-3-methyl-1-phenylsulfonyl-2-butanol

From 100 mg (0.52 mmol) of difluoromethyl phenyl sulfone, 0.15 mL (16 mmol) of 2-methylpropanal, 1.5 mL of dichloromethane, 1 mL of 50% aqueous sodium hydroxide, and 20 mg (0.050 mmol) of Aliquat 336 was obtained 137 mg (100% yield) of 1,1-difluoro-3-methyl-1-phenylsulfonyl-2-butanol as an oil: IR (neat) 3522, 3066, 2967, 1447, 1333, 1312, 1161, 1138, 1110, 1084, 1069, 1029, 996, 756, 714, 686, 634, 600, 591, 536 cm$^{-1}$; $^1$H NMR (CDCl$_3$) δ1.09 (apparent t, 6H, J=6 Hz), 2.05–2.45 (m, 1H), 3.13 (broad s, 1H), 4.39 (apparent dt, (H, J=22, 5 Hz), 7.50–8.13 (m, 5H) $^{19}$F NMR (CDCl$_3$, relative to CFCl$_3$) −106.9 ppm (dd, 1F, $J_{FF}$=235 Hz, $J_{HF}$=7 HZ), −115.6 ppm (ddd, 1F, $J_{FF}$=235 Hz, $J_{HF}$=22,8 Hz); mass spectrum (70 eV) m/e (relative intensity) 264 (2, M+), 143(37), 142(59), 125(25), 78(100), 77(80), 73(65), 55(37), 51(59), 43(86), 41(52), 39(31). Anal. Calcd. for C$_{11}$H$_{14}$F$_2$O$_3$S: C, 49.99; H, 5.34. Found: C, 50.98; H, 5.72.

EXAMPLE 10

1,1-Difluoro-3,3-dimethyl-1-phenylsulfonyl-2-butanol

From 100 mg (0.52 mmol) of difluoromethyl phenyl sulfone, 0.17 mL (16 mmol) of 2,2-dimethylpropanal, 1.5 mL of dichloromethane, 1 mL of 50% aqueous sodium hydroxide, and 20 mg (0.050 mmol) of Aliquat 336 was obtained 130 mg (90% yield) of 1,1-di-fluoro-3,3-dimethyl-1-phenylsulfonyl-2-butanol. Crystallization from toluene-hexane provided an analytical sample: mp 91°–94° C.; IR (KBr) 3505, 3057, 2969, 1479, 1449, 1347, 1328, 1314, 1280, 1158, 1119, 1092, 1080, 1042, 989, 756, 708, 687, 594, 527 cm$^{-1}$; $^1$H NMR (CDCl$_3$) δ1.10 (s, 9H), 3.22 (broad d, 1H), 4.14 (apparent dd, 1H, J=25, 4 Hz), 7.50–8.11 (m, 5H); $^{19}$F NMR (CDCl$_3$, relative to CFCl$_3$) −101.1 ppm (dd, 1F, $J_{FF}$=232 Hz, $J_{HF}$=2 Hz), −116.0 (dd, 1F, $J_{FF}$=232 Hz, $J_{HF}$=25 Hz); mass spectrum (70 eV) m/e (relative intensity) 278 (1, M+), 77(38), 57(100), 51(29), 41(50). Anal. Calcd. for C$_{12}$H$_{16}$F$_2$O$_3$S: C, 51.78; H, 5.80. Found C, 51.69; H, 5.77.

The novel substituted alcohols of this invention (formula I above) are of particular utility as intermediates in the synthesis of a variety of useful end products. The provision of these novel synthesis reactions constitutes another embodiment of this invention.

Among the synthesis reactions in which the products of formula I above may be utilized are desulfonylation reactions, oxidation reactions and fluorination reactions.

The desulfonylation reactions involve subjecting the formula I alcohol to suitable reducing conditions under which the following reaction is effected:

RCH(OH)CF$_2$SO$_2$Ar ⟶ RCH(OH)CHF$_2$
(I)                             (II)

Typical reduction systems for effecting this desulfonylation reaction include

Na, EtOH in tetrahydrofuran (THF)
Zn, NaOH in EtOH
Al(Hg), H$_2$O in THF
Na(Hg), phosphate buffer, MeOH The desulfonylated products (II) undergo many of the reactions to which secondary alcohols are amenable. One noteworthy reaction of this type is the reaction between compound (II) and a poly(dihalophosphazene) such as poly(dichlorophosphazene) whereby polymers of the formula

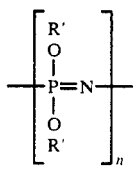

where R' is

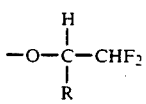

can be produced. These are useful thermoplastics for use in molding and extrusion of plastic objects having good high temperature stability. When compound II and one or more different alcohols or phenolic compounds are reacted with a poly(dihalophosphazene), elastomeric polymers are produced. When one different alcohol or phenolic compound (R"OH) is used, the resultant polymer may be represented by the formula

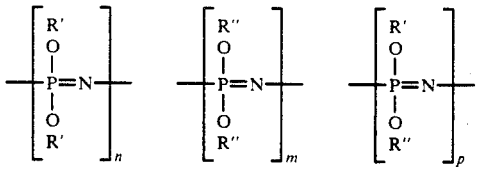

Examples 11–13 illustrate procedures that may be used to effect the foregoing desulfonylation reaction (conversion of I to II).

EXAMPLE 11

2,2-Difluoro-1-phenylethanol

Desulfonylation of 2,2-difluoro-1-phenyl-2-phenylsulfonylethanol to 2,2-difluoro-1-phenylethanol was accomplished at 25° C. using Zn powder and NaOH (10 parts by weight each) in ethanol, a reduction system described by Balfe et al., *J. Chem. Soc.*, 1951, 382. The yield from this reaction was not determined due to contamination of the product with co-products containing the phenylsulfonyl group.

EXAMPLE 12

2,2-Difluoro-1-phenylethanol

The procedure of Example 11 was repeated using as the reduction system aluminum amalgam in wet THF (see Corey et al., *J Am. Chem. Soc.*, 1965, 87, 1345). The desired reductive desulfonylation proceeded more cleanly than that of Example 11 but the reaction stops at about 50% conversion regardless of the amount o excess metal used.

EXAMPLE 13

2,2-Difluoro-1-(4-methylphenyl)ethanol

A solution of 2.0 g (6.4 mmol) of 2,2-difluoro-1-(4-methylphenyl)-2-phenylsulfonylethanol and 1.9 mL (32 mmol) of absolute ethanol in 20 L of dry tetrahydrofuran was treated with 0.74 g (32 mmol) of sodium spheres. After 90 minutes 1 mL of methanol followed by 1 mL of water were added to decompose unreacted sodium, and the mixture was poured into 100 mL of 1N HCl. The resulting aqueous mixture was extracted with three 50 m portions of dichloromethane. Combination, drying (MgSO$_4$), and concentration of the organic layers afforded an orange liquid which was short path distilled to give 0.54 g (49% yield) of 2,2-difluoro-1-(4-methylphenyl)ethanol; bp 58° C. at 0.6 torr (lit 60°–62° C. at 0.5–0.6 torr; DePuy et al., *J. Oro. Chem.*, 1974, 39, 878); mass spectrum (70 eV) m/e (relative intensity) 172 (17, M+), 121 (100), 93 (68), 91 (75), 77 (64), 65 (25), 51 (46), 39 (24).

The oxidation reactions as applied to alcohols of formula (I) result in the formation of the corresponding ketones:

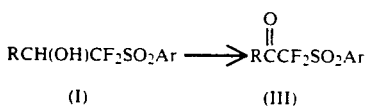

(I)    (III)

A particularly useful system for effecting this oxidation is a mixture of chromic and sulfuric acids. However any number of reagents that oxidize aldehydes to ketones are deemed suitable for effecting this reaction. Example 14 illustrates one way of performing this process.

EXAMPLE 14

Difluoro(phenylsulfonyl)methyl 4-Methylphenyl Ketone

A mixture of 0.03 g (0.96 mmol) of 2,2-difluoro-1-(4-methylphenyl-2-phenylsulfonylethanol, 0.78 g (1.4 mmol CrO$_3$) of Jones reagent (solution of 2.3 mL of 96% H$_2$SO$_4$, 10 mL of water, and 2.7 g CrO$_3$), and 3 mL of acetone was heated at reflux for 30 minutes. After cooling to room temperature the mixture wa treated with a little sodium bisulfite to discharge the yellow color and filtered. The filtrate was concentrated in vacuo to give a residue which was dissolved in dichloromethane and dried (MgSO$_4$). Removal of the solvent gave 0.28 g (95% yield) of difluoro(phenylsulfonyl)methyl 4-methylphenyl ketone. An analytical sample was obtained by crystallization from toluenehexane: mp 79°–81° C.; IR (KBr) 3071, 1684, 1605, 1446, 1352, 1314, 1277, 1146, 1084, 756, 687, 600, 564, 553, 527 cm$^{-1}$; $^1$H NMR (CDCl$_3$) δ2.42 (s, 3H), 7.28–8.14 (m, 9H); $^{19}$F NMR (CDCl$_3$, relative to CFCl$_3$) −102.3 ppm (s); mass spectrum (70 eV) m/e (relative intensity) 310 (3, M+), 119 (100), 91 (29), Anal. Calcd. for C$_{15}$H$_{12}$F$_2$O$_3$S: C, 58.05; H, 3.90. Found: C, 57.96; H, 4.19.

Ketones (III) may in turn be subjected to desulfonylatio conditions such as discussed above in connection with Examples 11–13 to produce ketones (IV) according to the equation:

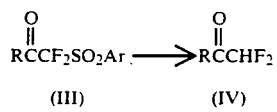

(III)    (IV)

In conducting this reaction care should be taken to avoid over reduction. Example 15 is illustrative.

EXAMPLE 15

Difluoromethyl p-tolyl ketone

A strip of aluminum foil weighing 43 mg was immersed in 2% solution of HgCl$_2$ in water for 25 seconds, washed successively with ethanol and diethyl ether, cut into small pieces, and added to an ice-cold solution of 50 mg of difluoro(phenylsulfonyl)methyl 4-methylphenyl ketone in 1 mL of 10% aqueous tetrahydrofuran. The heterogeneous mixture was stirred at 0°–5° C. for 5 hours and poured into 10 mL of 1NHC. Extraction of the resulting aqueous mixture with diethyl ether and GC/MS analysis of the organic layer indicated the presence of difluoromethyl p-tolyl ketone: mass spectrum (70 eV) m/e (relative intensity) 170(22, M+), 155(60), 119(100), 91(88), 65(37), 39(25).

Difluoromethyl ketones (IV) are of interest in the synthesis of antihypertensives. See in this connection. U.S. Pat. No. 4,483,870 to Kollonitsch et al., of Merck & Co., Inc.

Fluorination reactions to which the alcohols (I) may be subjected involve the following transformation:

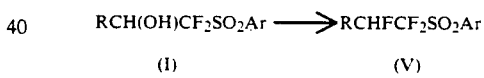

(I)    (V)

To effect this reaction, use may be made sulfur tetrafluoride, dimethylaminosulfur trifluoride or diethylaminosulfur trifluoride the latter two reagents being preferred because of their more agreeable properties and handling characteristics. Example 16 is illustrative of this process.

EXAMPLE 16

2-(4-Methylphenyl)-1-phenylsulfonyl-1,1,2-trifluoroethane

A solution of 0.24 mL (1.8 mmol) of diethylaminosulfur trifluoride in 5 mL of dichloromethane was cooled to −78° C. (dry ice-acetone bath) and treated dropwise with a solution of 0.50 g (1.6 mmol) of 2,2-difluoro-1-(4-methylphenyl)-2-phenylsulfonylethanol in 2 mL of dichloromethane. The cooling bath was removed and 30 minutes later 2 mL of saturated NaHCO$_3$ was added with vigorous stirring. The organic layer was removed, washed with on 2 mL portion of water, dried (MgSO$_4$), and concentrated in vacuo to give a residue which was crystallized from toluene-hexane, affording 0.36 g (71% yield) of 2-(4-methylphenyl)-1-phenylsulfonyl-1,1,2-trifluoroethane; mp 80°–82° C.; IR (KBr) 2924, 1447, 1352, 1185, 1163, 1117, 1054, 1013, 787, 757, 720, 686, 603, 567, 533, cm$^{-1}$; $^1$H NMR (CDCl$_3$) δ 2.36 (s, 3H), 6.10

(ddd, 1H, $J_{HF}$=44, 18, 5 Hz), 7.16–8.07 (m, 9H); $^{19}$F NMR (CDCl$_3$, relative to CFCl$_3$) −44.0 ppm (dt, 1F J=44, 16 Hz), −109.3 ppm (dd, 1F, J=247, 15 Hz), −118.8 ppm (dt, 1F, J=248, 17 Hz); mass spectrum (70 eV) m/e (relative intensity) 314 (11, M+), 172 (41), 123 (100), 77 (31). Anal. Calcd. for C$_{15}$H$_{13}$F$_3$O$_2$S: C, 57.32; H, 4.17. Found: C, 56.90; H, 4.47.

Under suitable conditions, compounds of the formula (V) will undergo an elimination reaction to produce $\alpha,\alpha,\beta$-trifluoro-1 olefinic compounds (VI) such as $\alpha, \alpha, \beta$-trifluorostyrenes and the like:

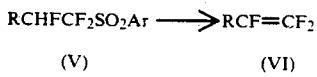

(V)  (VI)

Compounds (VI), especially $\alpha, \alpha, \beta$-trifluorostyrenes, are particularly useful as monomers and co-monomers in polymer production. See for example Antonucci in "Fluoropolymers"; Wall, Ed.; Wiley-Interscience; New York, 1972, Vol. XXV, Chap. 2, pp. 64–78.

Reagents and conditions for conducting difficult elimination reactions have been reported. See March, "Advanced Organic Chemistry", Wiley-Interscience; New York, 1985, pp. 913–916 (Sections 7-13 and 7-14). To date the best results in conducting the elimination reaction on (V) to form (VI) have been provided by using 1,8-diazabicyclo[5.4.0]undec-7-ene as the base. Example 17 illustrates this procedure.

EXAMPLE 17

1-(4-Methylohenyl)-1,2,2-trifluoroethene

A solution of 25 mg (0.080 mmol) of 2-(4-methylphenyl)-1-phenylsulfonyl-1,1,2-trifluoroethane and 60 μL (0.040 mmol) of 1,8-diazabicyclo[5.4.0]undec-7-ene in 0.5 mL of benzene was kept in an oil bath at 50°–60° C. for two hours. GC/MS analysis of the solution indicated the presence of a minor amount of starting material and a major amount of 1-(4-methylphenyl)-1,2,2-trifluoroethene: mass spectrum (70 eV) m/e (relative intensity) 172 (100, M+), 171 (37), 151 (30).

The yield was not determined in Example 17 because the product proved too sensitive to purify by preparative thin layer chromatography, and the reaction was not run at large enough scale to allow quantitative distillation.

This invention is susceptible to considerable variation within the spirit and scope of the appended claims.

What is claimed is:

1. Substituted alcohols of the formula

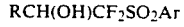

wherein R is pyridyl aliphatic or heterocyclic group, and Ar is an aryl group.

* * * * *